United States Patent
Schütze et al.

(10) Patent No.: US 7,044,008 B1
(45) Date of Patent: May 16, 2006

(54) COLLECTING DEVICE FOR COLLECTING OBJECTS THAT ARE DISSOLVED OUT OF A MASS, ESPECIALLY BY MEANS OF LASER RADIATION

(75) Inventors: Karin Schütze, Tutzing (DE); Raimund Schütze, Tutzing (DE)

(73) Assignee: P.A.L.M. Microlaser Technologies AG, Bernried (DE)

( * ) Notice: Subject to any disclaimer, the term of this patent is extended or adjusted under 35 U.S.C. 154(b) by 450 days.

(21) Appl. No.: 10/240,127

(22) PCT Filed: Sep. 15, 2000

(86) PCT No.: PCT/EP00/09073

§ 371 (c)(1), (2), (4) Date: Sep. 26, 2002

(87) PCT Pub. No.: WO01/73397

PCT Pub. Date: Oct. 4, 2001

(30) Foreign Application Priority Data

Mar. 27, 2000 (DE) ................................ 100 15 157

(51) Int. Cl.
*G01N 1/00* (2006.01)

(52) U.S. Cl. .................................. 73/863.01

(58) Field of Classification Search ............ 73/863.01, 73/864.31; 356/36; 435/40.5
See application file for complete search history.

(56) References Cited

U.S. PATENT DOCUMENTS 4,624,915 A   11/1986   Schindler et al.
4,907,158 A * 3/1990   Kettler et al. ............... 700/58
5,998,129 A   12/1999  Schütze et al.
6,100,051 A * 8/2000   Goldstein et al. .......... 435/40.5

FOREIGN PATENT DOCUMENTS

| DE | 25 05 774 A1 | 8/1976 |
| DE | 692 10 753 T2 | 10/1996 |
| DE | 695 10 925 T2 | 2/2000 |
| EP | 0 539 888 B1 | 5/1996 |
| EP | 0 748 439 B1 | 7/1999 |
| WO | WO-97/11156 | 3/1997 |
| WO | WO-97/13838 | 4/1997 |
| WO | WO-97/29354 | 8/1997 |
| WO | WO-97/29355 | 8/1997 |

(Continued)

OTHER PUBLICATIONS

Goldstein, Seth R., et al.; "An Instrument for Performing Laser Capture Microdissection of Single Cells"; Review of Scientific Instruments; Nov. 1999; pp. 4377-4385; vol. 70, No. 11; XP-000885106.

*Primary Examiner*—Charles Garber
(74) *Attorney, Agent, or Firm*—Squire, Sanders & Dempsey L.L.P.

(57) ABSTRACT

In order to allow automatic separation and recovery of biological or non-biological objects from a mass, which is located on a mount (3), by means of laser irradiation, a collecting apparatus (2) is proposed which has control means (7, 50) for automatic production of adjustment signals for the adjustment means (13), wherein the adjustment means adjust and hence position, as a function of these adjustment signals, a holding unit (19) having at least one collecting means (21) which is or are used for collecting an object which is released from the mass.

31 Claims, 5 Drawing Sheets

FOREIGN PATENT DOCUMENTS

| WO | WO-98/35216 | 8/1998 |
|----|-------------|--------|
| WO | WO-99/00658 | 1/1999 |
| WO | WO-99/28725 | 6/1999 |
| WO | WO-99/39176 | 8/1999 |

* cited by examiner

COLLECTING DEVICE FOR COLLECTING OBJECTS THAT ARE DISSOLVED OUT OF A MASS, ESPECIALLY BY MEANS OF LASER RADIATION

The present invention relates to a collecting apparatus for collecting or gathering biological or non-biological objects which are released from a mass which is located on a mount, as claimed in the precharacterizing clause of claim 1. The present invention relates in particular to a collecting apparatus such as this, the use of which enables biological or non-biological objects, which are cut out and/or catapulted out of a biological mass by means of laser irradiation, to be collected.

Suitable separating and sorting apparatuses are commercially available for separating individual cells from a large number of biological objects which are dispersed in a liquid. While electrostatic principles for spatial separation are used for fluorescence-activated cell sorting (fluorescent activated cell sorter, FACS), magnetic forces are used for magnetically activated cell sorting (magnetic activated cell sorter, MACS). In this case, however, the cells are not on a planar mount but are alongside one another. Furthermore, both methods have the disadvantage that some objects can be separated from one another only to a restricted extent (FACS) or not at all (MACS).

The methods described above cannot release, from a cell group, any individual cells such as a tissue or a histological tissue preparation.

WO 97/29355 A of the present applicant thus proposes a novel method for sorting and for recovering individual biological objects which are arranged on a planar mount. In particular, this document proposes that a selected biological object be separated from the surrounding further biological mass by means of a laser beam, so that the selected biological object is prepared free from the rest of the biological mass. The biological object prepared freely in this way is then catapulted by means of a laser shot from the mount to a collecting apparatus where it is collected and held, for example by a container (cap) in the form of a pot. It is likewise possible to catapult the selected biological object directly from the surrounding biological mass by means of a single laser shot to the collecting apparatus, so that there is no need for separate laser irradiation in order to cut out the desired biological object.

For the purposes of the present patent application, the expression Abiological object@ generally means, inter alia, living or fixed biological cells or cell components, which are a component of a liquid or solid biological material, such as a cell tissue, a scrape or a cell culture etc. However, the method described above can be used just as well for non-biological objects (non-living material) which may be, for example, microscopically small objects composed of glass, silica, plastic etc., or synthetically produced vesicles etc. in the biological mass. However, the present invention will be described in the following text on the basis of the preferred application area of the processing of biological objects, although it need not be restricted to this.

As has already been mentioned, a pot-shaped collecting vessel (cap) may be used for collecting or gathering the objects catapulted out of the appropriate biological mass by means of laser irradiation. The use of a collecting substrate or the like is likewise feasible, to which the catapulted-out objects adhere. Irrespective of which collecting means is or are actually used, the respective collecting means must always be positioned as exactly as possible with respect to the corresponding point in the biological mass which has been processed by means of laser irradiation. This is still true if the biological objects are not catapulted out of the biological mass by means of laser irradiation but are merely cut out by means of laser irradiation, pulled down from the respective mount by virtue of their weight, and must be collected by means of a suitable collecting means. In this case as well, the collecting means must be positioned as accurately as possible underneath the respective processing point in the biological mass.

According to the prior art, collecting apparatuses are known for this purpose which can be fitted above or underneath the mounting table of a corresponding laser microscope system, and which can be moved in the x, y and z directions. The collecting apparatus and/or the holder for the respective collecting means are/is in this case moved manually. However, this means that the collecting apparatus cannot be positioned with the necessary precision. The collecting apparatus can be positioned sufficiently accurately, but only with considerable effort.

The present invention is thus based on the object of providing a collecting apparatus for collecting objects which are released from a biological or non-biological mass, and which allows the collecting apparatus, and/or the respectively used collecting means, to be positioned as precisely as possible with as little effort as possible.

According to the invention, this object is achieved by a collecting apparatus having the features of claim 1. Each of the dependent claims define preferred and advantageous embodiments of the present invention.

The collecting apparatus according to the invention has a holding unit which is designed to hold at least one collecting means. In this case, the cap of a so-called Eppendorf or microcentrifuge container may, in particular, be used as the collecting means, and is held by the already described holding unit. Adjustment means are provided for adjusting the holding unit and/or the retention means which are provided to hold it, and these adjustment means are driven by control means in order to adjust the retention means and/or the holding unit appropriately, and hence to position the holding unit together with the holding means in the desired manner, as a function of adjustment signals which are produced by the control means.

The collecting means are thus positioned under computer control, and with high precision.

The adjustment means are preferably designed such that they can pivot the holding unit, together with the collecting means held by it, from a placement position to a working position, and vice versa. Furthermore, the adjustment means are preferably designed such that, even in the working position in which the collecting means can be observed by means of the microscope in the corresponding laser microscope system, the retention means and/or the holding unit held by it together with the collecting means can be adjusted parallel to the mount plane, in order to use the microscope to observe a biological or non-biological object which is located in the collecting means and has previously been released from the mass which is located in the mount plane. This not only allows an object which has been released from the mass to be collected by means of the collecting apparatus but also allows said object to be investigated in more detail, in order to find specific features of this object, without a separate apparatus being required for this purpose. A null position is preferably defined for the collecting means, with the adjustment means and/or the control means being designed such that automatic resetting to the predefined null position is possible after adjustment of the retention means and/or of the holding unit together with the collecting means in the x or y direction (which process is carried out in order to observe an object which is located in the collecting means), so that the original null position can also automatically be assumed once again after the object which is located in the collecting means has been moved away.

According to one exemplary embodiment of the present invention, the collecting apparatus is intended for holding and positioning an individual collecting means. In this case, the holding unit has an opening into which, by way of example, the cap of a microcentrifuge container can be inserted, as the collecting means. The retention means are preferably designed to be in a number of parts, in which case the collecting means can be positioned without any play and extremely precisely by means of a special magnetic bearing, while at the same time using a structure which is extremely flat. The holding unit together with the collecting means held in it can be adjusted by means of servo motors which, for example, are driven via a so-called joystick which includes automatic resetting to the null position. Servo motors may also be used for pivoting of the retention means, with the retention means in this case preferably being moved along an incline which ensures that, when the retention means are pivoted to the placement position, this at the same time results in movement away from the mount plane in the vertical direction.

According to a further exemplary embodiment of the present invention, the holding unit is designed to hold a large number of collecting means. In this case, it has been found to be particularly advantageous for a medium in the form of a slice, in particular a circular medium, with a number of openings distributed in the circumferential direction of this medium, to be used as the holding unit for holding the collecting means. The adjustment means may have a pivoting drive for pivoting the holding unit between the already mentioned placement position and the working position, as well as a rotary drive for positioning the respectively desired collecting means. The rotary drive may be used together with a further adjustment mechanism, which acts in the working position, in order to move away at the same time an object which is held in a holding means. Markings which are applied to the holding unit may be used to automatically find the null position of each collecting means once again, even after adjustment of a collecting means in the x and y directions. In principle, it is even sufficient to apply a single marking to the holding unit for this purpose since the individual openings for the collecting means or for the individual collecting means are in a predefined position with respect to one another.

The use of such a holding unit with a large number of collecting means makes it possible to quickly release a number of biological or non-biological objects successively from the mass to be processed, with one object in each case being collected by a corresponding collecting means. The individual collecting means may be moved over the mass to be processed successively in a rapid sequence with computer assistance, with in each case one object being conveyed into the corresponding collecting means, for example by catapulting by means of a laser shot. In this case, this computer-aided adjustment of the collecting apparatus and/or of its holding unit together with the collecting means held in it may be combined with, likewise computer-aided, laser irradiation of the mass so that previously selected objects in the mass can be released successively from the mass fully automatically, and can each be conveyed individually into the appropriate collecting means.

Although, for the purposes of the present patent application, the present invention will be explained on the basis of the preferred application of biological or non-biological objects being catapulted out of a biological mass by means of laser irradiation, it should be noted that, in principle, the present invention can also be applied to systems in which the collecting apparatus is located underneath the object mount, and in which the biological or non-biological objects are merely cut out of the surrounding biological mass by means of laser irradiation and fall, just by virtue of their weight, downward into the collecting apparatus or the appropriate collecting means. The present invention can also likewise be applied to non-biological masses, for example polymer masses etc., from which individual objects can be released by means of laser irradiation or the like. Finally, the present invention can also be used in situations in which the microscopically small objects to be collected are not released from the surrounding mass located on the mount by means of laser irradiation, but in any other way.

The present invention will be explained in more detail in the following text, with reference to the attached drawings and using preferred exemplary embodiments.

FIG. 1 shows the design of a laser microscope system, as can be used for a collecting apparatus according to the invention. The system is modular in design and can thus be individually matched to different experimental requirements.

Figure 1:
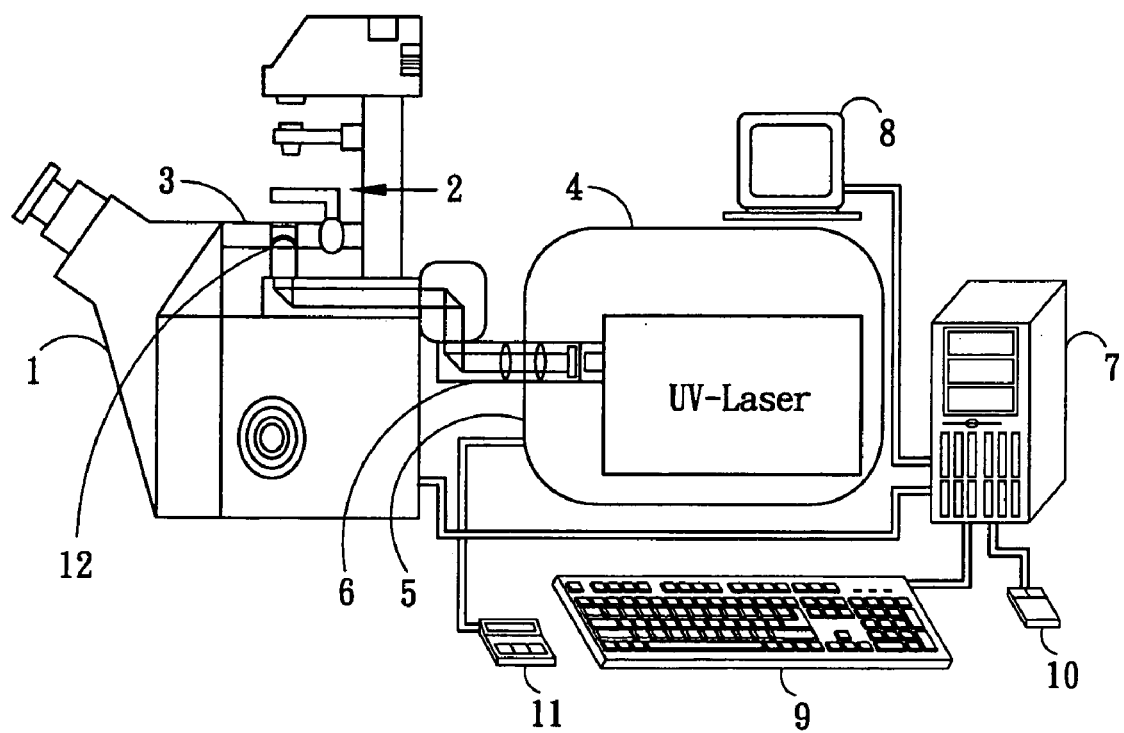
FIG. 1 shows the basic design of a laser microscope system, in which the collecting apparatus according to the invention can be used.

The system shown in FIG. 1 has a laser apparatus 4, in which a laser light source is accommodated, in order to produce a laser light beam. Optics 5, 6 are also accommodated in the laser apparatus 4, and these optics 5, 6 are required in order to input the laser beam into a microscope 1 and to adjust the laser focus in the object plane to the optical focus of the microscope 1. In the present case, this may be a pulsed UV nitrogen laser with a wavelength of 337 nm and a pulse energy of approximately 270 µJ, in which case the pulse duration may be 3 ms and the pulse repetition frequency 1–30 pulses per second. A control panel may be provided for controlling the laser apparatus 4, by means of which the laser energy and/or the laser focus can be set to desired values. The nitrogen laser emits a laser beam with a fixed laser energy. For precise adjustment of the laser energy, a quartz filter 5 is arranged at right angles to the laser beam path, whose position can be controlled as a function of the setting on the control panel, in order in this way to adjust the laser energy as appropriate. In this case, the quartz filter 5 may be adjusted automatically or manually. In addition to setting the laser energy, it is also possible to set the laser focus independently of the microscope focus, that is to say the focal point of the laser can be shifted in the z direction relative to the object plane of the microscope 1. The laser focus may also be adjusted as a function of the setting on the control panel, both automatically and manually, by means of appropriate movement of the lenses 6. The pulse rate of the laser can also preferably be set via said control panel, with an indication furthermore providing information about the settings on the control panel.

The laser beam is input via a number of coated beam splitters into the microscope 1, and is deflected toward an objective 12. The laser beam which is emitted via the objective 12 finally strikes a motorized and computer-controlled microscope or mounting table 3, on which is arranged an object mount with a biological mass that is to be processed. A collecting apparatus 2, which is likewise motorized and is preferably computer-controlled, is located above the mounting table 3. The components 2 and 3 allow exact object positioning with nanometric precision, and precise collecting of biological or non-biological objects which are catapulted out upward by means of laser irradiation from the mass which is located on the mounting table 3.

The microscope 1 may be a microscope of any desired configuration. In particular and in principle, the use of both an inverse microscope as well as a vertical microscope or a laser microscope is feasible. The microscope 1 is equipped with a video camera, in particular a CCD video camera (charge coupled device), which records the area of the object mount or mounting table 3 above the objective 12. The video signal from this video camera is supplied to a conventional computer (personal computer) 7 where it is processed using a so-called frame grabber card, so that the corresponding video image can be displayed in real time on the screen or monitor 8 of the computer 7. It is likewise possible to store individual video images on a memory medium in the computer 7. Furthermore, the computer 7 also allows an analogue or digital video recorder to be coupled, in order to record the video images supplied from the video camera.

Various functions which allow both computer-aided, that is to say automatic, driving of the laser apparatus 4 and of the microscope 1 and/or of the mounting table 3 and of the collecting apparatus 2, are implemented on the computer 7 or in the software running in it, so that, by way of example, the laser is activated automatically, and the collecting apparatus 2 as well as the mounting table 3 can be moved and adjusted automatically. Conventional input means, such as a keyboard 9, a computer mouse 10 or a trackball, joystick or the like (not shown) are provided for setting or selecting these functions.

Furthermore, the laser apparatus 4 has an associated foot-operated switch 11, whose operation allows the laser to be activated manually.

In order to cut the biological mass which is located on the object mount or on the mounting table 3, the user can preset a suitable cutting line with computer assistance, which is converted by appropriate driving of the laser apparatus 4 and of the mounting table 3 to an appropriate relative movement between the laser beam and the mounting table 3, so that, when the laser apparatus 4 is activated at the same time, the biological mass is cut along the predetermined cutting line by means of the laser beam. It is likewise possible, for example, to convert a movement of the computer mouse 10 directly to a corresponding movement of the mounting table 3, so that manual cutting can also be carried out, with the laser apparatus 4 being activated at the same time. It should be noted that, before a cutting process, the laser power and/or the laser focus must be adjusted appropriately as a function of the sample to be processed. As has already been explained above, this may be done via the control panel of the laser apparatus 4, or else with computer assistance.

A biological or non-biological object which has been cut out of the biological mass in this way can be catapulted by means of further laser irradiation out of the biological mass to the collecting apparatus 2 located above it. For this purpose, the objects to be catapulted out of the biological mass can be defined or marked with computer assistance, and the mounting table 3 can then be adjusted automatically such that the objects to be catapulted are automatically moved successively over the laser beam, and are each catapulted out of the object plane to the collecting apparatus 2 by setting a short laser shot. For this purpose, the laser energy must be manually or automatically increased in comparison to the laser energy used for cutting, and/or the laser beam must be manually or automatically defocused with respect to the laser beam used for cutting, in order to achieve the desired photon effect which leads to the desired object being shot out. The individual laser pulses or laser shots can be produced with computer assistance fully automatically as a function of the adjustment of the mounting table 3. A single laser pulse or laser shot can likewise be initiated by pressing briefly on the foot-operated switch 11 shown in FIG. 1.

In order to catapult selected objects, it is not absolutely essential for these object to have previously been cut out of the surrounding biological mass. In fact, experiments have shown that, in principle, it is also possible to catapult individual objects directly out of the surrounding biological mass by means of appropriate laser irradiation, provided the laser energy and/or the laser focus are set appropriately.

The collecting apparatus 2, which is located above the mounting table 3 or the object plane in the system illustrated in FIG. 1, has one or more collecting means which firmly hold an object which has been catapulted out of the object plane. By focusing the microscope 1 onto the collecting apparatus 2 or the respective collecting means, which are located in the light path of the microscope 1, of this collecting apparatus 2, the biological or non-biological object which has been catapulted out and is held by the corresponding collecting means can then be viewed and investigated via the microscope 1 or the screen 8 of the computer 7, with an adjustment capability to adjust the collecting apparatus 2 parallel to the object plane preferably being provided for this purpose, in order to make it possible to move away, the object that has been catapulted out using the microscope.

Figure 2:
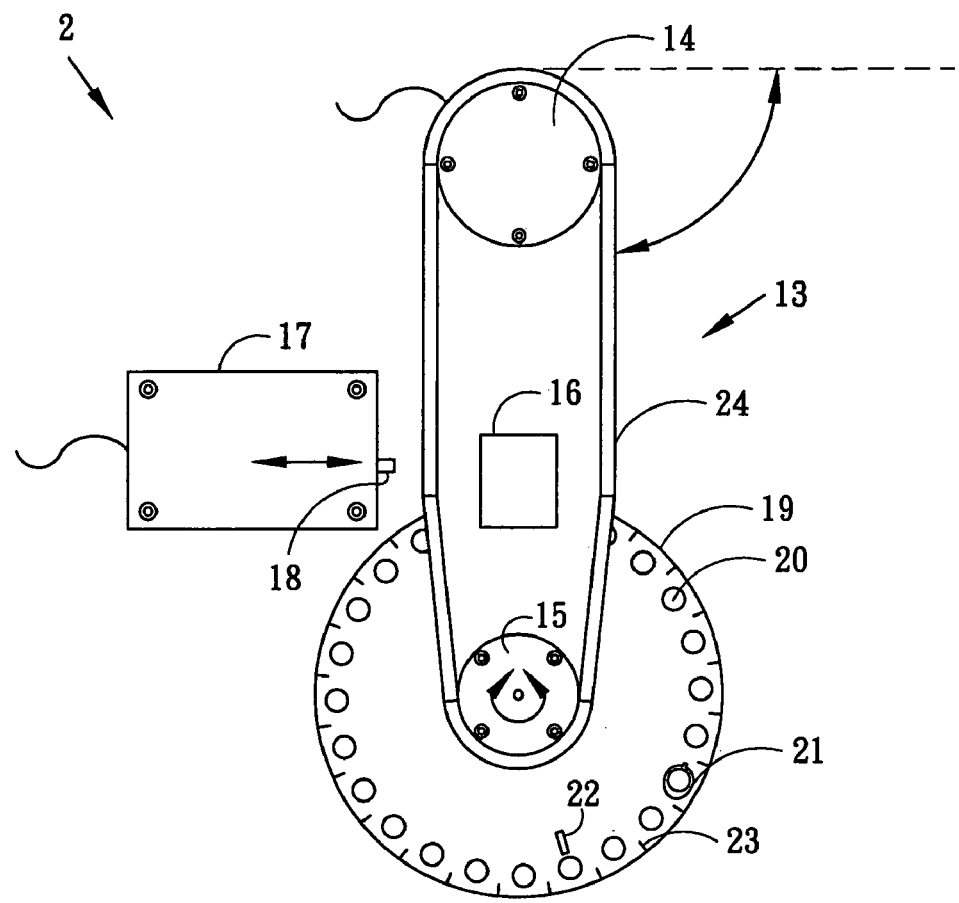
FIG. 2 shows a plan view of a collecting apparatus according to a first exemplary embodiment of the present invention.

FIG. 2 shows an exemplary embodiment of the collecting apparatus 2 illustrated in FIG. 1, which allows completely automatic positioning of a collecting means above the respective object to be catapulted out of the object plane. In particular, this exemplary embodiment is designed in such a way that a large number of biological or non-biological objects are catapulted out of the object plane successively, with computer assistance, and are each caught by appropriate collecting means, so that each object which is catapulted out is held by one collecting means. Since, in this way, each object which is catapulted out is associated with one, and only one, collecting means, the individual objects can subsequently be found again, and viewed, relatively easily.

The exemplary embodiment shown in FIG. 2 has a holder 24 for a holding unit 19, which holder 24 is used to hold a large number of collecting means 21. An adjustment apparatus 13 for adjusting the holder 24 and the holding unit 19 is integrated in the holder 24.

In the illustrated exemplary embodiment, the holder 24 is in the form of a retaining arm which is fitted, in some suitable way, to the stand or to the mounting table 3 of the microscope 1 that is shown in FIG. 1. The adjustment apparatus 13 has a pivoting drive 14 for pivoting the holder 24 between a working position, as illustrated in FIG. 2, and a placement position, as indicated by dashed lines in FIG. 2. In the working position, the holding unit 19 with the collecting means 21 is located at least partially above the object mount, which is located on the mounting table 3, while, in the placement position, the holding unit 19 is pivoted out of the light path of the microscope 1 and of the laser beam, so that individual collecting means can be inserted into the. holding unit 19 and can be removed from it again, or the holding unit 19 can be replaced. Furthermore, a rotary drive 15 is provided for rotating the holding unit 19, in order to make it possible to position a respectively designed collecting means in a predefined position above the object mount or the mounting table 3. The pivoting drives 14 and the rotary drive 15 can be driven via the computer 7 shown in FIG. 1.

In the exemplary embodiment illustrated in FIG. 2, the holding unit 19 is in the form of a preferably circular disk, for example composed of aluminum, which has circular openings 20 that are distributed in the circumferential direction and are at uniform distances apart. A suitable collecting means 21 may be inserted into each of these openings 20, allowing biological or non-biological objects which are catapulted out of the object plane to be collected and held. The collecting means 21 may be—as is shown in FIG. 2—in particular the cap of a so-called Eppendorf or microcentrifuge container, in which case, in the arrangement of the collecting apparatus 2 as shown in FIG. 1 above the mounting table 3, the opening in the cap can be inserted downward into the holding unit 19 as illustrated in FIG. 2, so that an object which has been catapulted out upward from the object plane or the mounting table 3 remains attached to the inside of this cap 21. In order to support the object which has been collected in this way, the cap 21 may once again be placed on the associated microcentrifuge container.

The holding unit 19 is held, preferably removably, on the holder 24 in some suitable way, so that the entire holding unit 19 can easily be detached from the holder 24. The holder 24 and the holding unit 19 may be coupled, for example, pneumatically, magnetically or mechanically, with the holding unit 19 that is shown in FIG. 2 then fitted at its center to the holder 24, such that it can be detached or removed.

If the holder 24 together with the holding unit 19 held on it and with the collecting means 21 located in the holding unit 19 are located in the working position, as illustrated in FIG. 2, above the mounting table 3, a desired collecting means 21 can be positioned, by suitable actuation of the rotary drive 15, above the respective object to be catapulted out of the biological mass that is located on the mounting table 3. In particular, computer-aided actuation of the rotary drive 15 in conjunction with computer-aided actuation of the mounting table 3 makes it possible for a previously selected biological or non-biological object to be positioned successively above the laser beam and, in a corresponding manner, for a desired collecting means 21 to be positioned above the object that is to be catapulted out and is located in the object plane. Finally, the previously selected object is catapulted out of the object plane into the collecting means located above it, and is held there, by subsequent activation, preferably likewise automatic activation, of the laser in the form of a short laser impulse or laser shot. This allows, in particular, a large number of objects to be catapulted fully automatically out of the biological mass located on the mounting table 3, with the rotary drive 15 being adjusted after each catapulting process such that each object which is catapulted out is collected and held by a different collecting means 21, predetermined with computer assistance.

In order to record the instantaneous position of the holding unit 19, a sensor 16 or sensor logic, which is likewise connected to the computer 7 shown in FIG. 1, is integrated in the holder 24. In the illustrated exemplary embodiment, this is, in particular, an optical sensor 16 which records markings 22 and 23 located on the holding unit 19 and, in this way, can always uniquely define the current rotary position of the holding unit 19 and can identify collecting means, and/or the correspondingly associated opening 20, located at that instant above the object that is to be catapulted out. In principle, it is sufficient for the holding unit 19 to have only one marking 22, which may be recorded by the sensor 16, with the sensor 16 then recording the adjustment of the rotary drive 15 with respect to that position at which the marking 22 is located with respect to the sensor 16, so that it is uniquely possible to deduce the instantaneous rotary position of the holding unit 19.

If a collecting means 21 located above the object mount or the mounting table 3 has collected an object catapulted out of the biological mass, it is worthwhile, for many applications, observing the object that has been catapulted out, using the microscope 1 shown in FIG. 1, by appropriately focusing the microscope 1 onto the respective collecting means 21. In order to allow the object that is located in the respective collecting means 21 to be moved away completely using the microscope, the already mentioned adjustment apparatus 13 is designed such that, in the already mentioned working position, the respective collecting means 21 can be adjusted with high precision in the x and y directions, so that the object which has been catapulted out and is located in the respective collecting means 21 can be moved completely through the light path of the microscope 1. The adjustment in the x direction is in this case carried out by means of a pin 18, which projects out of a suitable drive unit 17, which is likewise connected to the computer 7. This pin 18 is used firstly as a stop for the holder 24 in the working position. Secondly, by adjusting the pin 18 in the direction of the arrow, the holder 24 and hence also the holding unit 19 together with the collecting means 21 to be observed can be moved with high precision in the x direction. It is likewise feasible for the adjustment in the x direction to be carried out via the pivoting drive 14. In contrast, the adjustment in the y direction can be provided via the rotary drive 15, in which case the area to be viewed using the microscope 1 can also be moved in the y direction by slightly rotating the holding unit 19, and hence the collecting means 21 to be observed. In this way, the drives 14 and/or 15, which are provided for adjustment of the holder 24 in any case, can at the same time be used to observe an object located in a collecting means 21 and/or to move away the object located in the collecting means 21.

Once the holder 24 and the holding unit 19 that is held on it, together with the collecting means 21 located in it, have been adjusted as described above in order to observe an object located in the collecting means 21, it is frequently desirable for the collecting means 21 to assume the original position once again after observation and after the object which has been caught has been moved away. A reset function is provided for this purpose, which allows the collecting means 21 and the holding unit 19, which has the collecting means 21, and the holder 24 to be reset automatically to the original position. This reset function can be implemented in such a way that each collecting means or the corresponding opening 20 in the holding unit 19 has a specific associated null position, which may, in particular, correspond to that position in which the respective collecting means 21 is located centrally above the object to be catapulted out, that is to say, in general, also centrally above the laser beam of the laser apparatus 4. This null position may be stored for each opening 20 and/or for each collecting means 21, in the computer 7. After adjustment of the holder 24 and of the holding unit 19 held on it, and/or of a collecting means 21 located in it, in order to observe an object which is located in the collecting means 21, this null position can be called up once again, so that the drives 14, 15 and 17 are actuated appropriately in order to automatically reset the corresponding collecting means 21 to the null position.

In order to collect a number of objects which have been catapulted out of the biological mass, the collecting means 21, which are held in the individual openings 20 in the holding unit, are generally rotated successively in the clockwise direction or in the counterclockwise direction, so that another collecting means 21 is in each case positioned successively above the respective object to be catapulted out. In this case, in order to simplify the control capacity, it is also possible to use the null position, as determined for a preceding collecting means 21 corresponding to the rotation direction of the holding unit 19, for a subsequent collecting means 21. In principle, it is fundamentally sufficient to define the null position for only one opening 20 or one collecting means 21, and to store this, provided the individual openings 20 and the collecting means 21 held in them are in a predefined position with respect to one another, as shown in FIG. 2, since the null positions of the other collecting means 21 can be derived uniquely from the predetermined null position of one collecting means 21.

The holding unit 19 shown in FIG. 2 may particularly advantageously be in the form of a disposable article, in which case the holding unit 19 is offered ready-fitted with a number of collecting means 21 (caps).

Figure 3:
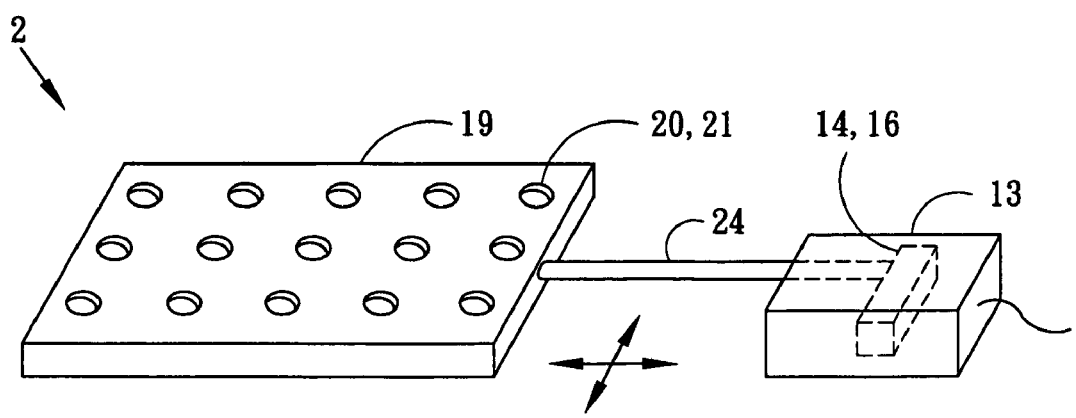
FIG. 3 shows a perspective view of a collecting apparatus according to a second exemplary embodiment of the present invention.

FIG. 3 shows a further exemplary embodiment of the present invention, in which the depressions (wells) 20 in a so-called microtiter plate 19 are used as the collecting means. The collecting apparatus 2 shown in FIG. 3 is, in particular, a collecting apparatus which can be used in conjunction with a vertical microscope, with the collecting apparatus 2 being positioned underneath the mounting table 3 or the object plane, and the laser beam striking the object mount from above, in order to catapult individual objects, from the biological mass located on the lower face of the object mount, downward out of the object plane. This collecting apparatus 2 is likewise suitable for collecting individual biological or non-biological objects which fall out of the biological mass just by virtue of their weight, as a consequence of the force of gravity after being cut out of the biological mass.

In the exemplary embodiment shown in FIG. 3, the holder 24 is in the form of a rod and is adjusted together with the microtiter plate 19, which is held by it, in the direction of the arrow in the x and y directions by means of a suitable adjustment apparatus 13. The adjustment apparatus 13 is once again driven with computer assistance and has components which correspond to the functions of the drives 14 and 15, as illustrated in FIG. 2, as well as the functions of the sensor or sensor logic 16 (for monitoring and defining the instantaneous position of the microtiter plate 19). Furthermore, in the exemplary embodiment illustrated in FIG. 3, each opening 20, which is at the same time used as the collecting means 21, can be positioned deliberately such that an object which is released from the biological mass can be collected. Suitable containers, for example microcentrifuge containers, may also be inserted into the openings 20, so that an object which is released from the biological mass falls directly into one such container.

Figure 4:
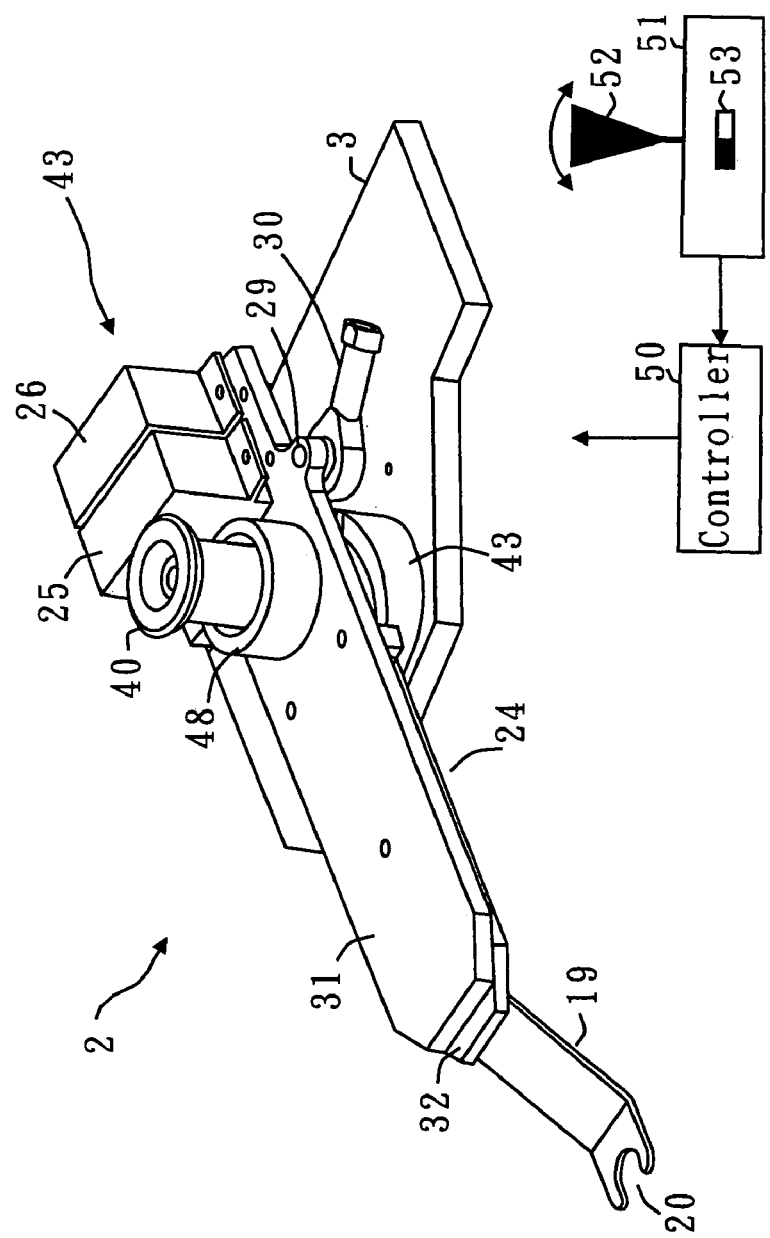
FIG. 4–FIG. 6 show perspective views of a collecting apparatus according to a third exemplary embodiment of the present invention.
Figure 5:
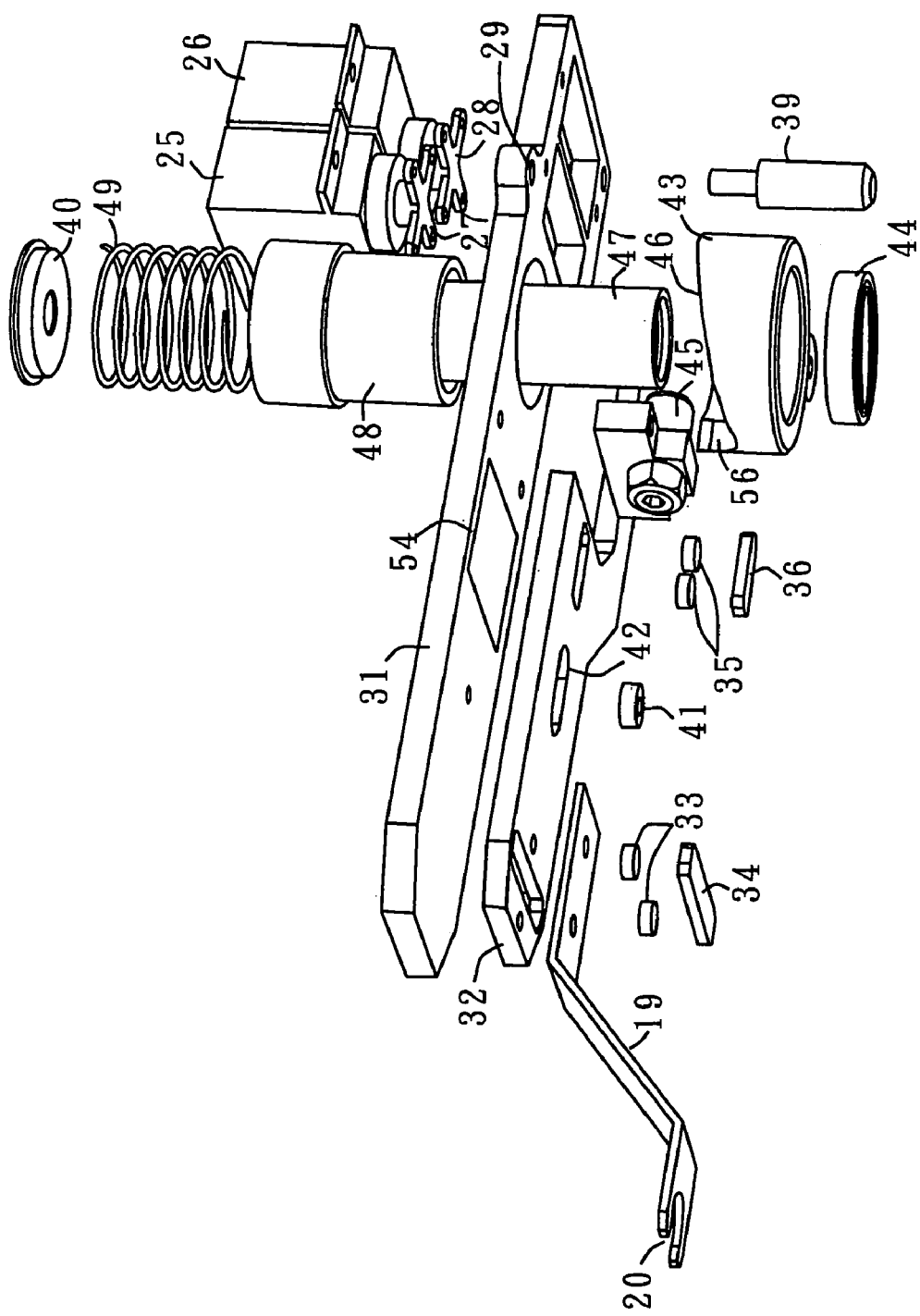
Figure 6:
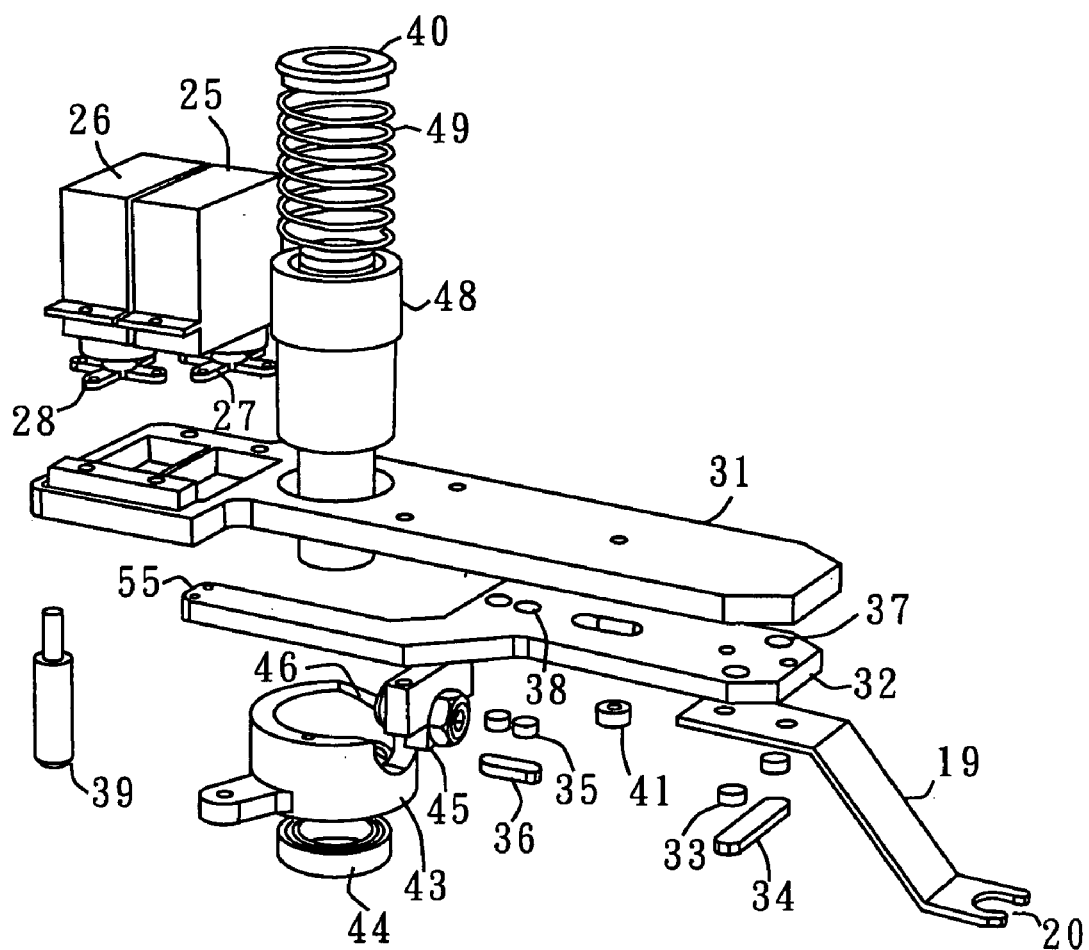

FIGS. 4–6 show various perspective views of a third exemplary embodiment of the present invention. This is, in particular, a collecting apparatus 2 which is provided for positioning only one collecting means. However, this exemplary embodiment may, of course, also be modified such that a number of collecting means can be held, and can be positioned analogously to FIGS. 2 and 3, at the same time.

The exemplary embodiment which is illustrated in FIGS. 4–6 has a web-like holding unit 19 which, at its front end, has an opening 20 into which, for example and analogously to FIG. 2, the cap of a microcentrifuge container can be inserted. The exemplary embodiment which is illustrated in FIGS. 4–6 is designed, in particular as shown in FIG. 1, for use in a so-called inverse microscope, in which the collecting apparatus 2 is mounted in some suitable way above the respective mounting table 3 of the microscope 1. In consequence, the respectively used collecting means can be inserted, with its opening pointing downward, into the opening 20 in the holding unit 19. The exemplary embodiment which is illustrated in FIGS. 4–6 may, of course, easily be modified such that it is suitable for use in vertical microscopes 1.

The holder 24, which is provided for holding the holding unit 19 together with the collecting means located in it, is designed in a number of parts in the illustrated exemplary embodiment. The holding unit 19 is held on a first retaining part 32, which is in turn held on a second retaining part 31. Magnets 33 and 35, respectively, with a corresponding respective yoke 34 or 36, are used as the retention means. The magnets 33 are inserted into openings 37 in the first retaining part 32, with the holding unit 19 being positioned between the first retaining part 32 and the yoke 34. The yoke 34 closes the magnetic circuit, so that the holding unit 19 is held on the first retaining part 32 by means of the yoke 34. The magnets 35 are inserted into openings 38 in the first retaining part 32, and the yoke 36 is fitted in a corresponding manner, so that, once again, a magnetic circuit is closed. The magnets 33 and the yoke 34 as well as the magnets 35 and the yoke 36, and the respective magnetic circuits formed by them, allow the first retaining part 32, together with the holding unit 19 located on it, to be held just by means of magnetic forces on the lower face of the second retaining part 31.

Servo motors 25, 26, on whose lower face respective drives 27 and 28 project, are mounted at the rear end of the second retaining part 31. These drives 27, 28 are connected via suitable means to the second retaining part 31 such that the second retaining part can be adjusted in the x direction, for example by means of the drive 27, and the second retaining part 31 can be adjusted in the y direction by means of the drive 26. In this context, FIG. 6 shows, merely by way of example, openings 55 at the rear end of the first retaining part 32, which, for example, are connected via wires to the two drives 27 and 28.

The first retaining part 32 together with the holding unit 19 located on it can thus be moved with respect to the second retaining part 31 in a simple manner, by virtue of the magnetic bearing which acts between the two retaining parts 32 and 31, by appropriately driving the servo motors 25 and 26, respectively. A sheet 54 (for example a Teflon sheet) is preferably fitted on the lower face of the second retaining part 31 which, for example, can be manufactured from iron in the same way as the first retaining part 32 and the holding unit 19, thus allowing the first retaining part 32 to be moved with respect to the second retaining part 31 with as little friction as possible.

Furthermore, a projection or a pin 41 is fitted to the lower face of the second retaining part 31, and projects into an elongated hole 42 formed in the first retaining part 32. The first retaining part 32 can thus be moved with respect to the second retaining part 31 only within the boundaries defined by the elongated hole 42. However, as can be seen, the magnetic bearing that is provided not only allows the first retaining part 32 to be moved longitudinally, but also allows the first retaining part 32 to be rotated and/or to be moved laterally, with respect to the second retaining part 31, with the projection 41 acting as a center of rotation in this case.

The magnetic bearing described above can thus be used for the already mentioned search function when the servo motors 25, 26 are driven automatically, when an object which has been catapulted out of the biological mass is located in the collecting means held by the holding unit 19, in order to make it possible to observe this object in more detail with the aid of the respectively used microscope, and to allow it to be moved away. In this case, the chosen form of bearing allows, in particular, the holding unit 19, and the collecting means held by it, to be adjusted with high precision, and without any play. Further, the magnetic bearing ensures that the entire collecting apparatus can be produced such that it is extremely flat.

As has already been mentioned, the servo motors 25 and 26, which are used to adjust the first retaining part 32 together with the holding unit 19 located on it, with respect to the second retaining part 31, are driven automatically. In this case, an input means may be used, which automatically converts a user input to corresponding control signals for the servo motors 25, 26. This input means is, in particular, designed such that it records any movement applied by a user and converts this to the control signals for the servo motors 25, 26 such that this results in the first retaining part 32, together with the holding unit 19 located on it, being adjusted in a corresponding manner to the movement of the user. A joystick 51, as shown in FIG. 4, may be used, by way of example, as the input means for this purpose, with the movement of the lever 52 of this joystick 51 being automatically converted by a controller 50 to corresponding control signals for the servo motors 25, 26.

The use of a joystick 51 for adjusting the first retaining part 32 and the holding unit 19 that is held on it is also advantageous in that the lever 52 in conventional joysticks is prestressed by means of suitable internal spring mechanisms in the direction of the initial position of the lever 52 as shown in FIG. 4. This means that, when the lever 52 is moved and the lever 52 is subsequently released, the lever 52 automatically returns back to its original position, and the controller 50 drives the servo motors 25, 26 such that the first retaining part 32 is likewise reset in a corresponding manner back to the original position. The initial position of the lever 52 as shown in FIG. 4 may thus be regarded as the null position for the first retaining part 32 and for the collecting means which are held by the holding unit 19, with an appropriate resetting process being carried out automatically after the adjustment of the collecting means and/or of the holding unit 19 and of the first retaining part 32. This is advantageous for the reasons explained in particular with reference to FIG. 2. If automatic resetting to the null position is not desired, this can be deactivated by means of a switch 53, as is worthwhile, for example, in order to investigate specific features of the object which has been collected and which may be viewed only by adjustment of the holding unit 19.

The already described servo motors 25, 26 are used for high-precision adjustment of the first retaining part 32 and of the holding unit 19, which is held on it, when the collecting apparatus 2 is in the working position, that is to say when a collecting means which is held by the holding unit 19 is located above the object plane or above the laser beam. The collecting apparatus or the holder 24 may also be pivoted between the working position and a placement position in the exemplary embodiment illustrated in FIGS. 4–6. In the placement position, a suitable collecting means can be inserted into the opening 20 in the holding unit 19, and can be removed from this opening 20, or the holding unit 19 can be replaced, with the collecting means (when in the placement position) being located outside the light path of the laser, and preferably also outside the light path of the microscope 1. The pivoting mechanism which is used for pivoting the holder 24 will be explained in more detail in the following text.

As can be seen in particular from FIGS. 5 and 6, a roller 45 is attached to the lower face of the first retaining part 32 and is mounted on an obliquely running contact surface 46 of a base part 43. At its lower end, a sleeve 48 has a diameter which is designed such that the sleeve fits through a corresponding circular opening in the second retaining part 31. At the upper end, the sleeve 48 has a further diameter which, in particular, is larger than the diameter of the circular opening in the second retaining part 31, so that the upper end of the sleeve 48 rests on the second retaining part 31 in the assembled state (as shown in FIG. 4). An element 47 which is in the form of a piston is passed through the sleeve 48 and is closed at the upper end by a cover 40, and at the lower end by a cover 44. The sleeve 48 contains a spiral spring 49, which prestresses the sleeve 48 downward, that is to say toward the base part 43. As is shown in FIG. 4, a corresponding pivoting mechanism 30 can act on an opening 29 in the second retaining part 31 and, by way of example, is likewise driven by means of computer-aided servo motors.

It is assumed that the collecting apparatus 2 is located in its working position in the illustration shown in FIG. 4, so that a collecting means which is held in the opening 20 in the holding part 19 is located above the biological mass to be processed. If an appropriate force is now exerted on the pivoting mechanism 30, the second retaining part 31 and hence the entire holder 24 together with the holding part and the collecting means held on it are pivoted in the counterclockwise direction, until the already mentioned placement position is reached. The placement position may, for example, be defined by a stop, which is provided with respect to the lower end of the second retaining part 31. This stop is indicated schematically by way of example in the form of a bolt 39, which is fitted to the second retaining part 31, in FIG. 5 and FIG. 6.

During the pivoting of the holder 24 together with the holding part 19 in the counterclockwise direction, the roller 45 which is attached to the lower face of the first retaining part 32 at the same time runs upward on the obliquely running contact surface 46 of the base part 43, so that this not only results in a pivoting movement but, at the same time, the entire holder 24 together with the holding part 19, the collecting means held in it and the sleeve 48, which is inserted into the second retaining part 31, are raised upward against the spring force of the spiral spring 49. The placement position is thus reached by means of a combined pivoting and lifting movement. The spring force of the spiral spring 49 prestresses the sleeve 48, and hence also the entire holder 24, downward. This makes it easier for the holder 24 together with the holding part 19 to move back to the working position. The working position is defined uniquely by a stop 56 for the roller 45, which stop 56 is formed in the contact surface 46 of the base part 43 (as shown in FIG. 5). In the working position, the collecting means which are held by the holding unit 19 are located merely at a distance of about 0.5–10 mm above the object mount or the mounting table 3.

The pivoting movement may be assisted by means of ball bearings or the like, which act in the interior of the sleeve 48 and, in particular, between the inner face of the sleeve 48 and the outer face of the element 47, which is in the form of a piston.

The invention claimed is:

1. Collecting apparatus for collecting objects which are released, in particular by means of laser irradiation, from a mass which is located on a mount (3), having a holding unit (19) for holding at least one collecting means (21) for collecting an object which is released from the mass, and having adjustment means (13) for adjusting the holding unit (19) in order in this way to position the holding unit (19), characterized in that control means (7, 50) are provided for automatic production of adjustment signals for the adjustment means (13), in that the adjustment means (13) are designed such that they automatically adjust the holding unit (19) in accordance with the adjustment signals from the control means (7, 50), in that the adjustment means (13) are designed such that when appropriate adjustment signals from the control means (7) are present they move, in particular pivot, the holding unit (19) from a placement position which is intended for fitting the holding unit (19) to the collecting apparatus (2) or for fitting the collecting means (21) to the holding unit (19), to a working position which is used for collecting an object which is released from the mass, or vice versa, and in that the adjustment means have a first adjustment device (14) for pivoting the holding unit (19) from the placement position to the working position, or vice versa, and in that the adjustment means (13) have a second adjustment device (15, 17, 25, 26), in order to adjust the holding unit (19) in the working position essentially parallel to the plane of the mount (3).

2. The collecting apparatus as claimed in claim 1, characterized in that the collecting apparatus (2) is designed such that, in the placement position, the holding unit (19) together with the collecting means (21) is further away, in particular raised, from the mount (3) having the mass, than in the working position.

3. The collecting apparatus as claimed in claim 2, characterized in that retention means (24) are provided for holding the holding unit (19), in that the retention means (24) are mounted on an obliquely running contact surface (46) such that the retention means (24) are moved along the obliquely running contact surface (46) while the retention means (24) are being pivoted from the working position to the placement position and, in the process, the retention means (24) are moved away from the mount (3) in the vertical direction.

4. The collecting apparatus as claimed in claim 1, characterized in that the adjustment means (13, 17) are designed such that, in the working position, they allow automatic adjustment of the holding unit (19) essentially parallel to the plane of the mount (3) in order to view, using a microscope, the object collected by the collecting means (21).

5. The collecting apparatus as claimed in claim 4, characterized in that a null position is defined for the collecting means (21) in the working position, and in that the control means (7, 50) are designed such that, after adjustment of the holding unit (19) together with the collecting means (21) held by it, from the null position, by means of appropriate actuation of the adjustment means (13, 17), said control means (7, 50) automatically reset to the null position the holding unit (19) together with the collecting means (21) held by it.

6. The collecting apparatus as claimed in claim 4, characterized in that retaining means (24) are provided for holding the holding unit (19), in that the retention means (24) have a first retaining part (32) with the holding unit (19) held thereon and a second retaining part (31) with a magnetic bearing (33, 35) acting between the first retaining part (32) and the second retaining part (31), and wherein the adjustment means (13, 25, 26) acts on the first retaining part (32) in the working position in order to adjust the holding unit (19), to move with respect to the second retaining part (31) by means of the magnetic bearing (33, 35), the first retaining part (32) together with the holding unit (19) that is held by it.

7. The collecting apparatus as claimed in claim 6, characterized in that a sliding layer (54) is provided between the first retaining part (32) and the second retaining part (31).

8. The collecting apparatus as claimed in claim 6, characterized in that a projection (41) is provided on the lower face of the second retaining part (31), and projects into an elongated hole (42) which is formed in the first retaining part (32).

9. The collecting apparatus as claimed in claim 6, characterized in that the control means (7, 50) drive the adjustment means (13, 25, 26) as a function of any movement applied by the user, as detected by the input means (51), such that the first retaining part (32), together with the holding unit (19) held by it, is shifted with respect to the second retaining part (31) in a corresponding manner to the movement applied by the user.

10. The collecting apparatus as claimed in claim 4, characterized in that the holding unit (19) is designed to hold a large number of collecting means (21), and in that identification means (16) are provided, in order to identify the position of the individual collecting means (21) in the working position.

11. The collecting apparatus as claimed in claim 10, characterized in that the holding unit (19) has at least one marking (22, 23), and in that the identification means (16) are designed such that, by monitoring the marking (22, 23), they deduce the position of the individual collecting means (21) in the working position.

12. The collecting apparatus as claimed in claim 1, characterized in that the holding unit (19) is held by retaining means (24) and can be removed from the retention means (24).

13. The collecting apparatus as claimed in claim 1, characterized in that the holding unit (19) is designed to hold a large number of collecting means (21).

14. The collecting apparatus as claimed in claim 1, characterized in that input means (51) are provided for detecting any movement applied by a user, and in that the control means (7, 50) are designed such that they convert any movement applied by a user, as detected by the input means (51), to corresponding adjustment signals for the adjustment means (13, 25, 26), in order to move the holding unit (19) in a corresponding manner to the movement applied by the user.

15. The collecting apparatus as claimed in claim 1, characterized in that the holding unit (19) is designed to hold a large number of collecting means (21), and in that the control means (7) are designed such that, by producing appropriate adjustment signals for the adjustment means (13), they position a specific collecting means (21) in order to collect an object which is released from the mass.

16. The collecting apparatus as claimed in claim 1, characterized in that the holding unit (19) is designed to hold a large number of collecting means (21), in that a number of objects which can be released from the mass are defined, and in that the control means (7) are designed such that, by producing appropriate adjustment signals for the adjustment means (31), they automatically adjust the holding unit (19) such that different collecting means (21) are positioned successively in order to collect a respectively predefined object which is released from the mass.

17. The collecting apparatus as claimed in claim 1, characterized in that the holding unit (19) is designed to hold a large number of collecting means (21), in which case the collecting means (21) can be fitted to the holding unit (19) distributed in the circumferential direction, and in that the second adjustment device has a rotary drive (15) for rotating the holding unit (19) essentially parallel to the plane of the mount (3) which has the mass.

18. The collecting apparatus as claimed in claim 1, characterized in that the second adjustment device has an adjustment mechanism (17) with an adjustment pin (18), which, firstly, is used as a stop in the working position and, secondly, appropriately adjusts the holding unit (19) in the working position when the adjustment pin (18) is moved.

19. Collecting apparatus for collecting objects which are released, in particular by means of laser irradiation, from a mass which is located on a mount (3), having a holding unit (19) for holding at least one collecting means (21) for collecting an object which is released from the mass, and having adjustment means (13) for adjusting the holding unit (19) in order in this way to position the holding unit (19), characterized in that control means (7, 50) are provided for automatic production of adjustment signals for the adjustment means (13), in that the adjustment means (13) are designed such that they automatically adjust the holding unit (19) in accordance with the adjustment signals from the control means (7, 50), and in that the adjustment means (13, 17) are designed such that, in the working position, they allow automatic adjustment of the holding unit (19) essentially parallel to the plane of the mount (3) in order to view, using a microscope, the object collected by the collecting means (21).

20. The collecting apparatus as claimed in claim 19, characterized in that a null position is defined for the collecting means (21) in the working position, and in that the control means (7, 50) are designed such that, after adjustment of the holding unit (19) together with the collecting means (21) held by it, from the null position, by means of appropriate actuation of the adjustment means (13, 17), said control means (7, 50) automatically reset to the null position the holding unit (19) together with the collecting means (21) held by it.

21. The collecting apparatus as claimed in claim 19, characterized in that retaining means (24) are provided for holding the holding unit (19), in that the retention means (24) have a first retaining part (32) with the holding unit (19) held thereon and a second retaining part (31) with a magnetic bearing (33, 35) acting between the first retaining part (32) and the second retaining part (31), and wherein the adjustment means (13, 25, 26) acts on the first retaining part (32) in the working position in order to adjust the holding unit (19), to move with respect to the second retaining part (31) by means of the magnetic bearing (33, 35), the first retaining part (32) together with the holding unit (19) that is held by it.

22. The collecting apparatus as claimed in claim 19, characterized in that the holding unit (19) is designed to hold a large number of collecting means (21), and in that identification means (16) are provided, in order to identify the position of the individual collecting means (21) in the working position.

23. Collecting apparatus for collecting objects which are released, in particular by means of laser irradiation, from a mass which is located on a mount (3), having a holding unit (19) for holding at least one collecting means (21) for collecting an object which is released from the mass, and having adjustment means (13) for adjusting the holding unit (19) in order in this way to position the holding unit (19), characterized in that control means (7, 50) are provided for automatic production of adjustment signals for the adjustment means (13), in that the adjustment means (13) are designed such that they automatically adjust the holding unit (19) in accordance with the adjustment signals from the control means (7, 50), and in that the holding unit (19) is held by retaining means (24) and can be removed from the retaining means (24).

24. The collecting apparatus as claimed in claim 23, characterized in that retaining means (24) are provided for holding the holding unit (19), in that the retention means (24) have a first retaining part (32) with the holding unit (19) held thereon and a second retaining part (31), and wherein the adjustment means (13, 25, 26) acts on the first retaining part (32) in the working position in order to adjust the holding unit (19), to move with respect to the second retaining part (31), the first retaining part (32) together with the holding unit (19) that is held by it.

25. Collecting apparatus for collecting objects which are released, in particular by means of laser irradiation, from a mass which is located on a mount (3), having a holding unit (19) for holding at least one collecting means (21) for collecting an object which is released from the mass, and having adjustment means (13) for adjusting the holding unit (19) in order in this way to position the holding unit (19), characterized in that control means (7, 50) are provided for automatic production of adjustment signals for the adjustment means (13), in that the adjustment means (13) are designed such that they automatically adjust the holding unit (19) in accordance with the adjustment signals from the control means (7, 50), and in that the holding unit (19) is designed to hold a large number of collecting means (21).

26. The collecting apparatus as claimed in claim 25, characterized in that the control means (7) are designed such that, by producing appropriate adjustment signals for the adjustment means (13), they position a specific collecting means (21) in order to collect an object which is released from the mass.

27. The collecting apparatus as claimed in claim 25, characterized in that the holding unit (19) is designed to hold a large number of collecting means (21), in that a number of objects which can be released from the mass are defined, and in that the control means (7) are designed such that, by producing appropriate adjustment signals for the adjustment means (31), they automatically adjust the holding unit (19) such that different collecting means (21) are positioned successively in order to collect a respectively predefined object which is released from the mass.

28. The collecting apparatus as claimed in claim 25, characterized in that the holding unit (19) is designed to hold a large number of collecting means (21), and in that identification means (16) are provided, in order to identify the position of the individual collecting means (21) in the working position.

29. The collecting apparatus as claimed in claim 28, characterized in that the holding unit (19) has at least one marking (22, 23), and in that the identification means (16) are designed such that, by monitoring the marking (22, 23), they deduce the position of the individual collecting means (21) in the working position.

30. Collecting apparatus for collecting objects which are released, in particular by means of laser irradiation, from a mass which is located on a mount (3), having a holding unit (19) for holding at least one collecting means (21) for collecting an object which is released from the mass, and having adjustment means (13) for adjusting the holding unit (19) in order in this way to position the holding unit (19), characterized in that control means (7, 50) are provided for automatic production of adjustment signals for the adjustment means (13), in that the adjustment means (13) are designed such that they automatically adjust the holding unit (19) in accordance with the adjustment signals from the control means (7, 50), in that input means (51) are provided for detecting any movement applied by a user, and in that the control means (7, 50) are designed such that they convert any movement applied by a user, as detected by the input means (51), to corresponding adjustment signals for the adjustment means (13, 25, 26), in order to move the holding unit (19) in a corresponding manner to the movement applied by the user.

31. The collecting apparatus as claimed in claim 30, characterized in that retaining means (24) are provided for holding the holding unit (19), in that the retention means (24) have a first retaining part (32) with the holding unit (19) held thereon and a second retaining part (31), and wherein the adjustment means (13, 25, 26) acts on the first retaining part (32) in the working position in order to adjust the holding unit (19), to move with respect to the second retaining part (31), the first retaining part (32) together with the holding unit (19) that is held by it, and in that the control means (7, 50) drive the adjustment means (13, 25, 26) as a function of any movement applied by the user, as detected by the input means (51), such that the first retaining part (32), together with the holding unit (19) held by it, is shifted with respect to the second retaining part (31) in a corresponding manner to the movement applied by the user.

* * * * *